United States Patent
Daniels

(12)
(10) Patent No.: US 6,495,530 B1
(45) Date of Patent: Dec. 17, 2002

(54) COMPOSITION FOR TREATING A PATIENT SUSCEPTIBLE TO OR SUFFERING FROM A CARDIOVASCULAR DISORDER OR DISEASE

(75) Inventor: Bruce A. Daniels, Oklahoma City, OK (US)

(73) Assignee: Endomatrix, Inc., Napa, CA (US)

( * ) Notice: Subject to any disclaimer, the term of this patent is extended or adjusted under 35 U.S.C. 154(b) by 22 days.

(21) Appl. No.: 09/851,545

(22) Filed: Jun. 8, 2001

Related U.S. Application Data

(62) Division of application No. 09/302,690, filed on Apr. 30, 1999, now Pat. No. 6,255,296, which is a continuation-in-part of application No. 08/585,743, filed on Jan. 16, 1996, now abandoned, which is a continuation of application No. 08/180,131, filed on Jan. 11, 1994, now abandoned.

(51) Int. Cl.[7] ............................................. A01N 43/04
(52) U.S. Cl. ...................... 514/56; 514/561; 514/564; 514/822; 514/824
(58) Field of Search ...................... 514/56, 561, 564, 514/822, 824

(56) References Cited

U.S. PATENT DOCUMENTS

| | | | | |
|---|---|---|---|---|
| 3,574,832 A | * | 4/1971 | Engel et al. | 424/183 |
| 5,260,066 A | | 11/1993 | Wood | |
| 5,428,070 A | * | 6/1995 | Cooke et al. | 514/557 |
| 5,482,925 A | * | 1/1996 | Hutsell | 514/11 |

OTHER PUBLICATIONS

Dobosz et al., Scand.J.Clin.Lab.Invest., 56(7), 657–663 (1996).*

Luescher et al, J.Cardiovasc.Pharmacol., 24(suppl. 3), S16–S26 (1994).*

* cited by examiner

*Primary Examiner*—Sreeni Padmanabhan
(74) *Attorney, Agent, or Firm*—Ali Kamarei; Draper B. Gregory

(57) ABSTRACT

The present invention is directed to a composition comprising a therapeutically effective amount of exogenous heparin and arginine or physiologically acceptable salts thereof which is used in the treatment and prevention of cardiovascular diseases or disorders.

4 Claims, No Drawings

COMPOSITION FOR TREATING A PATIENT SUSCEPTIBLE TO OR SUFFERING FROM A CARDIOVASCULAR DISORDER OR DISEASE

CROSS-REFERENCE TO RELATED APPLICATIONS

This is a divisional application mandated by the U.S. Patent and Trademark Office in application 09/302,690 (filed Apr. 30, 1999 now U.S. Pat. No. 6,255,296 in which certain method claims were allowed and for which an issue fee has already been paid in full, said application Ser. No. 091302, 690 being a continuation-in-part application of U.S. patent application Ser. No. 08/585,743 (filed on Jan. 16, 1996 now abandoned which is a continuation of U.S. patent application Ser. No. 08/180,131 (filed on Jan. 11, 1994), now abandoned.

STATEMENT REGARDING FEDERALLY SPONSORED RESEARCH

Not Applicable.

REFERENCE TO A MICROFICHE APPENDIX

Not Applicable.

FIELD OF THE INVENTION

This invention relates generally to a formulation for treating a patient susceptible to or suffering from a cardiovascular disorder or disease, and more particularly, but not by way of limitation, to a formulation for preventing and treating atherosclerosis, arteriosclerosis, congestive heart failure, arterial stenosis, re-stenosis, smooth muscle cell. hypertrophy, cardiac cell hypertrophy, thrombogenicity, clotting disorders, platelet disorders, myocardial infarction, cerebrovascular ischemia, peripheral vascular ischemia, angina pectoris or hypertension.

BACKGROUND OF THE INVENTION

Cardiovascular disorders and diseases, and their associated complications are a principal cause of disabilities and deaths of individuals in the United States and Western Europe. For example, in recent years more than 500,000 deaths have occurred annually in the United States alone as a result of coronary artery disease, and an additional 700,000 patients have been hospitalized for myocardial infarction.

There has been an ongoing search for effective long term treatment for disorders and diseases of the heart and arteries, such as atherosclerosis, arteriosclerosis, congestive heart failure, angina pectoris, and other disorders and diseases associated with the cardiovascular system. Prior treatments for such disorders or diseases include administration of vasodilators, angioplasty and by-pass surgery, for example. Such treatments have met with great disapproval due to risks versus benefits gained by the various treatments. Such treatments have serious shortcomings in long-term effectiveness. The use of vasodilator drugs and mechanical treatments for acute and chronic occlusive vascular diseases of the heart, central and peripheral vascular systems have to date been ineffective for favorable long-term results. The outcome with current treatments is minimally impacted because the treatments are directed toward effects of the underlying disease process rather than initial molecular cause of the disease or disorder.

For example, the rationale for vasoactive drugs is to reduce blood pressure by acting directly or indirectly on vascular and/or cardiac smooth muscle, thereby decreasing vascular resistance to flow. Such drugs do not treat initial cause of elevated pressure and abnormal flow. Rather, they seek to reduce the resulting effect of the disease or disorder. Such drugs activate the sympathetic nervous system by way of a baroreceptor reflex to produce an increased heart rate and force of myocardial contraction which are not beneficial effects. Other side effects from such drugs include headache, heart palpitations, anxiety, mild depression, dry-mouth, unpleasant taste in the mouth, nausea, vomiting, angina, myocardial infarction, congestive heart failure, decreased cardiac output, fluid retention, fatigue, and weakness. Pharmacological treatment is not specific in its effect on the initial molecular cause of the disease activity, and treats a limited spectrum of effects in the diseases which are multifactorial.

As a further example, improved outcome in atherosclerotic vascular diseases is seen with cholesterol reduction and drug treatment for lipid disorders. These treatments do not prevent cellular or molecular reactions attributed to platelets, macrophages, neutrophils, lymphocytes, smooth muscle cells, and other cell types known to be involved in atherosclerosis and complications of the disease.

Likewise, thrombolytic therapy, angioplasty and bypass surgery have been minimally successful long-term. Current mechanical and pharmacological treatments focus on a partial or completely occluded vessel where, at the particular site, it is either unclogged or bypassed with connecting vessels. These treatments fail to address physiologic derangements of homeostatic systems which allow the occlusive process to begin and progress. Accordingly, there is frequent recurrent occlusion in the initially treated vessel, as well as microembolism from incomplete resolution of thrombus at the occlusive site treated; and no treatment for sites not judged to be adequately occluded or stenotic.

There remains a great need for treatment which prevents failure of homeostatic controls and which restores these controls once derangements begin to develop. Restoration of endogenous regulatory systems and cellular domains to a healthy state prevents stenosis, occlusion, thrombosis, and thromboembolic processes which occur as a consequence of such derangements. Continuous and episodic restoration of control in molecular processes which finely regulate homeostasis, prevent atherosclerosis, variants thereof, hypertension, congestive heart failure, macro and microthrombosis and thromboembolism, myocardial infarction, cerebrovascular accident, and complications of these disease processes.

SUMMARY OF THE INVENTION

It is a conception of the inventor that a cellular matrix composed of heparin-arginine-water polymers is responsible for controlling molecular milieu comprising the human cellular environment. It is these polymers which determine the protein distribution, functionality, DNA-RNA transcription regulation, and the physical properties of cells.

It is an object of the present invention to provide a composition of material comprised of exogenous heparin and arginine or functional analogs or physiologically acceptable salts thereof, which is directed to preventing and minimizing dysfunctional atomic and molecular interactions within human cellular environments and membranes, such interactions being associated with cardiovascular disease or disorders, by co-administration of said composition, in which components of the endothelium are stimulated to therapeutically modulate adverse molecular reactions associated with cardiovascular disease or dysfunction.

It is another object of the present invention to provide a composition of material which is directed to retarding adverse consequences of free radicals generated in human cellular domains relating to cardiovascular disease or disorders, by co-administration of exogenous heparin and arginine or functional analogs or physiologically acceptable salts thereof.

It is still a further object of the present invention to trigger an endogenous heparin production cycle within human cellular environments and membranes by co-administration of exogenous heparin and arginine or functional analogs or physiological acceptable salts thereof.

It is still a further object of the present invention to provide a composition of material which is directed to decreasing thrombogenicity, repairing cellular processes, and improving blood flow properties that are associated with thrombosis and hypoxia within a human cellular environment, by co-administration of exogenous heparin and arginine or functional analogs or physiologically acceptable salts thereof.

It is an object of the present invention to avoid known side effects such as thrombocytopenia and bleeding attendant with the administration of heparin alone, by co-administration of heparin and arginine.

It is a further object of the invention to provide a composition of material comprised of exogenous heparin and arginine or functional analogs or physiologically acceptable salts thereof, in co-administered therapeutic doses for human beings, which is directed to treatment and prevention of cardiovascular disease or disorders.

DETAILED DESCRIPTION OF THE PREFERRED EMBODIMENT

The present invention is directed to a formulation for inhibiting cardiovascular disorder or disease in a patient susceptible to or suffering from cardiovascular disorder or disease. In accordance with the invention, a patient susceptible to or suffering from a cardiovascular disorder or disease such as atherosclerosis, arteriosclerosis, congestive heart failure, arterial stenosis, re-stenosis, smooth muscle cell hypertrophy, cardiac cell hypertrophy, thrombogenicity, clotting disorders, platelet disorders, myocardial infarction, cerebrovascular ischemia, peripheral vascular ischemia, angina pectoris or hypertension, is treated with a therapeutically effective amount of a first substance characterized as exogenous heparin or its functional analogs or physiologically acceptable salts, and a second substance characterized as exogenous arginine or its functional analogs or physiologically acceptable salts thereof.

A therapeutically effective amount of heparin is defined primarily by clinical response in a patient, and ranges from about 2,000 IU to 200,000 IU daily, on variable schedule.

For example, the heparin is characterized such that it should be an amount sufficient to exert anti-thrombotic effects and less than an amount to cause hemorrhaging, while effectively maintaining integrity and functionality of the cellular membranes and surrounding environments.

A therapeutically effective amount of arginine ranges from 500 mg to 50,000 mg daily dependent on the underlying condition and nature of the physiological processes requiring treatment. For example, the arginine should be a sufficient amount (1) to sustain a level of nitric oxide to keep various cell types from dysfunctional activation states in the patient, (2) to increase prostacyclin secretion, (3) to reduce secretion of extra-cellular proteins and heparin binding proteins, and (4) to bind to available sulfate and carboxyl groups on heparin in order to increase extra-cellular matrix barrier properties which in turn decrease extra-cellular matrix pore size and permeability.

Again, effective doses of heparin vary with the particular patient condition and the method of administration. For example, it is noticed that subcutaneous injection of heparin results in greater concentration in the cellular and membrane domains than by intravenous injection.

Arginine, as used herein is L-arginine, and is added together with or separately from the heparin. L-arginine also includes sulfates thereof and sulfates of their functional analogs.

The physiological condition of the patient will largely dictate the required dosages and frequencies of arginine administration, i.e. weight, age, disease, sex.

The compound of the present invention can be formulated for oral, sublingual, subcutaneous, intravenous, transdermal or rectal administrations in dosages and in admixture with pharmaceutical excipients or vehicles including implanation or controlled-release devices.

For example, the compound of heparin and arginine can be dispersed in a physiologically acceptable, non-toxic liquid vehicle, such as water. Alternatively, the compound can be given in tablet, capsule, powder, granules or coated tablet form. The compound can be made in a conventional manner, and may be mixed with conventional pharmaceutical auxiliaries, such as binders, fillers, preservatives, tablet disintegrators, flow regulators, plasticizers, wetting agents, dispersants, emulsifiers, solvents, retarding agents and/or anti-oxidants. It also can be contained or complexed with lipids in various formulations and molecular arrangements, e.g. lipid tubules.

An efficiently operating homeostatic system is crucial to cellular function within mammalian organisms. In a healthy state, there is formed a gel matrix of heparin, arginine and water polymers, which houses a plurality of other molecules by accommodating dynamic binding of and release of such molecules without reaching concentration levels which destroy the gel structure and its regulatory functionalities.

Commercially, heparin is normally derived from animal tissue such as livers and lungs of cattle, bovine species and sheep.

Heparin and heparin-like compounds have also been found in plant tissue where the heparin or heparin-like compound is bound to the plant proteins in the form of a complex. Heparin and heparin-like compound derived from plant tissue are of particular importance because they are considerably less expensive than heparin and heparin-like compounds harvested from animal tissue.

Plants which contain heparin or heparin-like compounds such as physiologically acceptable salts of heparin, or functional analogs thereof will provide a suitable source for the present invention. Typical plant sources of heparin or heparin-like compounds include artemisia princeps, nothogenia fastigia (red seaweed), copallina pililifera (red algas), cladophora sacrlis (green seaweed), chaetomorpha anteninna (green seaweed), aopallina officinalis (red seaweed), monostrom nitidum, laminaria japonica, filipendula ulmaria (meadowsweet), ecklonia kuroma (brown seaweed), ascophyllum nodosum (brown seaweed), ginkgo biloba, ulva rigida (green algae), stichopus japonicus (seacucumber), panax ginseng, spiralina maxima, spirulina platensis, laurencia gemmifera (red seaweed), larix (larchwood), and analogs thereof.

Such plants are considered to be an effective and efficient source of heparin or heparin-like compounds for use in the present invention.

Polymer strands are an organizing determinant for membranes, proteins, receptors, ion channels, cell organelles, nuclear membranes, membrane pores, and other complex cellular constituents. The polymers organize water into arenas for confining bilipid layer membranes, for example, creating cell turgor and form and limiting hydrolytic properties of water on other molecular structures.

Heparin's high sulfate content imparts a high negative charge which attracts and binds positively charged substances like basic amino acids, basic domains of proteins and peptides, cations, water and other such charged molecules.

Arginine has a high positive charge and strongly associates with heparin along membrane surfaces such as endothelium and basement membranes and in association with water, organize as gel matrix.

The gel may be in a constant state of change, including transitions from one state or phase to another. As such, conformation can change and derangements occur as different substances move in and out of the gel and as the gel properties change.

A healthy gel matrix is formed from endogenous heparin, endogenous arginine and water.

The health gel structure has a conformation that preferentially supports interaction and binding of foreign molecules. The capacity to accommodate intrusions of such molecules before the gel structure collapses and loses its functionality is an important characteristic of the gel system.

An example of polar molecules that heparin binds and inactivates thereby modulating their activity, are serine proteases, other clotting factors and thrombolytic agents, antithrombin-thrombin, complement, apo-lipoproteins, growth-promoting factors, mitogens, heparinase, lipoprotein lipase, growth-inhibiting factors, chemotactic factors, super oxide dismutase, cytokines, numerous enzymes, and cytoskeletal proteins such as fibronectin.

As these intrusions accumulate locally or in a distributed fashion, they cause an interference within the gellular association of heparin and arginine. The interference can cause the gel structure to deteriorate, thus increasing its porosity or collapse altogether in a localized or distributed fashion. In addition, the intrusion may trigger a release of other bound polar molecules, such as calcium which would induce a non-homeostatic event.

These intrusions result in a displacement of arginine and decreased generation of nitric oxide as an additional effect. Intrusions limit the binding capacity of the heparin for argue and other molecules within the gel.

In order to reverse this disruption of the gel matrix caused by removal of arginine and/or heparin, the present invention employs a composition to maintain and rejuvenate the gel matrix and its functionality. In this regard, the present invention utilizes a full range of molecular weight heparin and arginine to give optimal pore closure and stabilization, and number and distribution of binding sites, wherein signaling, anti-proliferation, anti-thrombotic, anti-coagulant properties are maintained. Thus, the homeostatus-promoting functionalities of heparin, arginine, and heparin-arginine-water gel matrix, resultant from the herein-described composition, retard continuous and accumulative injury to cellular domains. By his retarding effect, cholesterol accumulations, generally referred to as "arterial plaques" are minimized. Heparin and arginine co-administration also leads to increased lipoprotein and lipase release with beneficial effects on plaque stability, growth, rupture, and regression.

The expression of endogenous heparin is surface receptor dependent in that the prostacyclin, in association with heparin at the gel surface, generates a signal to the golgi apparatus to produce endogenous heparin. Added exogenous heparin accumulates at the blood/endothelium surface thereby reconstituting the prostacyclin receptors which may have been damaged and depleted over time. Nitric oxide production at or near the same surface occurs from nitric oxide synthase action on exogenous and endogenous arginine substrate. This nitric oxide amplifies the signal by increasing the local concentration of prostacyclin, whose production is mediated by the nitric oxide.

Thus, heparin is generated in quantities sufficient to allow reassociation of arginine and heparin and restore the gel structure, as well as releasing or rearranging potentially injurious molecules in the gel matrix.

Addition of heparin to the gel system protects the functionality of the arginine in the gel, and addition of arginine to the gel system protects the functionality of heparin in the gel. In the extragellular medium, the ability of heparin to bind and quiesce molecules is augmented by simultaneous addition of exogenous heparin and exogenous arginine, wherein exogenous heparin is binding to extragellular potentially-intruding molecules, thus allowing existing gellular heparin to associate with gellular arginine. Exogenous arginine becomes the more available substrate for nitric oxide synthase, thereby protecting gellular endogenous arginine from the nitric oxide synthase activity and allowing the endogenous arginine to continuously re-associate with the gellular heparin, thus protecting the gel functionality.

Nitric oxide produced from arginine is an important physiological mediator. The enzyme responsible for nitric oxide production, nitric oxide synthase, requires CA++ and Calmodulin. The functionality of the heparin-arginine gel includes its binding and regulation of CA++ and Calmodulin. By regulating Calmodulin activity, the heparin-arginine gel regulates nitric oxide synthase activity responsible for nitric oxide production. Anti-clotting, clotting and thrombolytic molecules and other Calmodulin-mediated enzyme activations are regulated similarly by the gel.

The binding of water, small anions and cations within the heparin-arginine-water gel is facilitated by pi-bonding properties inherent in the saccharide ring structure within the heparin polymers. Changes in the shared electron density and electrical charge variation regulate the state of solvation and conformation of the gel polymers. Thus, small anion and cation binding induces changes in the state of solvation, changes in catalytic and hydrolytic properties of water, and changes in capacity of the gel to bind water and other molecules.

Low to high molecular weight heparin preferably having a high degree of sulfation, can be used as well as standard heparin as is commercially available. Human, animal, and recombinant heparin sources are believed to be useful in practicing the invention and are capable of stimulating the full range of responses claimed herein. The source of exogenous heparin, including the possibility of human recombinant heparin, and the source of arginine impart no special or additional properties to the homeostatic functionalities observed for those individual elements or their conjoined, synergistic functionalities. Various glycosaminoglycans, similar to heparin, are subject to in vivo epimerization and sulfation resulting from agents which promote acylation reactions and sulfation reactions, such as acetyl salicylic acid, thereby producing heparin or heparin functionality. Thus, for example, heparin sulfate is considered an analog of heparin. Heparin can be used in the form of its salts with physiologically tolerated bases, for example, sodium, calcium, magnesium, diethylamine, triethylamine or triethanolamine. Promoters of increased heparin production, such as prostacyclin, are the functional equivalent of heparin, as would be analog's thereof, such as taprostene and may be employed in the present invention.

Endothelial cell injury and myocardial cell injury occur from free radicals. Heparin binds super oxide dismutase which absorbs high energy electrons and deactivates free radicals. Heparin and nitric oxide bind free radicals preventing damage to enidothelial cells.

Congestive heart failure is in part due to free radical injury to myocardial cells. Heparin, super oxide dismutase and nitric oxide all attack and neutralize free radicals, therefore, diseases associated with cellular injury from free radicals are effectively treated and prevented by the present invention. Also, heparin aids in the reconstruction of damaged tissue by complexing and removing extracellular matrix protein accumulations, e.g. fibronectin with consequent reverse of organ hypertrophy states.

Heparin, via its association with arginine, enhances regeneration of endothelium following an injury to an endothelium surface.

It will be readily apparent to those skilled in the art that many modifications, derivations and improvements are within the scope of the invention. Such modifications, derivations, and improvements should be accorded full scope of protection by the claims appended hereto.

I claim:

1. A composition of material for treatment of cardiovascular disease comprising a mixture of arginine and heparin in therapeutic proportions.

2. A composition of material described in claim 1 comprising a mixture of physiologically acceptable salts of arginine and/or heparin.

3. A composition of material for treatment of endothelium dysfunction associated with cardiovascular disease comprising a mixture of arginine and heparin in therapeutic proportions.

4. A composition of material described in claim 1 comprising a mixture of physiologically acceptable salts of arginine and/or heparin.

* * * * *